United States Patent [19]
Grützke et al.

[11] Patent Number: 5,641,873
[45] Date of Patent: Jun. 24, 1997

[54] PROCESS FOR PREPARING ALKYL OLIGOGLYCOSIDES

[75] Inventors: Jürgen Grützke, Bochum; Stefan Schmidt, Haltern, both of Germany

[73] Assignee: Huels Aktiengesellschaft, Marl, Germany

[21] Appl. No.: 524,804

[22] Filed: Sep. 7, 1995

[30] Foreign Application Priority Data

Sep. 7, 1994 [DE] Germany .................. 44 31 853.7

[51] Int. Cl.$^6$ .................. G07G 3/00; G07H 1/06
[52] U.S. Cl. .................. 536/18.6; 536/18.5; 536/124
[58] Field of Search .................. 536/18.6, 18.5, 536/124

[56] References Cited

U.S. PATENT DOCUMENTS

| | | | |
|---|---|---|---|
| 5,206,357 | 4/1993 | Schmidt | 536/18.6 |
| 5,227,480 | 7/1993 | Oberholz et al. | 536/18.5 |
| 5,374,716 | 12/1994 | Biermann et al. | 536/18.6 |
| 5,420,262 | 5/1995 | Schmidt | 536/18.6 |
| 5,461,144 | 10/1995 | Kahsnitz et al. | 536/18.6 |

FOREIGN PATENT DOCUMENTS

| | | |
|---|---|---|
| 0 362 671 | 4/1990 | European Pat. Off. . |
| 0 514 627 | 11/1992 | European Pat. Off. . |
| 0 514 628 | 11/1992 | European Pat. Off. . |
| WO93/10133 | 5/1993 | WIPO . |

*Primary Examiner*—John Kight
*Assistant Examiner*—Everett White
*Attorney, Agent, or Firm*—Oblon, Spivak, McClelland, Maier & Neustadt, P.C.

[57] ABSTRACT

The preparation of alkyl oligoglycosides by transglycosidation of $C_2$ to $C_6$ alkyl glycosides using $C_8$ to $C_{20}$ fatty alcohols is improved by the fact that the fatty alcohol is preheated to at least 80° C., it is mixed with the alkyl glycoside, then the reaction is performed and $C_2$ to $C_6$ alcohol is flashed off under vacuum after the reaction. Products having a good color are obtained. Encrustation and cracking in the equipment do not occur.

17 Claims, No Drawings

PROCESS FOR PREPARING ALKYL OLIGOGLYCOSIDES

BACKGROUND OF THE INVENTION

1. Field of the Invention

The invention relates to a novel process for preparing alkyl oligoglycosides which have $C_8$ to $C_{20}$ alkyl chains by acid-catalyzed transglycosidation of $C_2$ to $C_6$ alkyl glycosides using $C_8$ to $C_{20}$ fatty alcohols.

2. Discussion of the Background

Alkyl oligoglycosides having $C_8$ to $C_{20}$ alkyl groups can be prepared in whole or in part from renewable raw materials. Therefore, and also because of their very good biodegradability, they are becoming increasingly important. In addition to their surfactant properties of interest, the products have the advantage that their polarity can be set exactly via the length of the alkyl chain and via the degree of glycosidation. By this means the alkyl oligoglycosides can be specifically directed to their field of application.

In the two-stage alkyl oligoglycoside preparation, a glycosidation is first carried out. Alkyl glycosides having short-chain alkyl groups are prepared from saccharides and $C_2$ to $C_6$ alcohols in this stage. These products are then converted in the second stage by transglycosidation using $C_8$ to $C_{20}$ alcohols into the desired alkyl oligoglycosides having surfactant properties.

This preparation route has long been known. Recent applications in this sector frequently concern the preparation of products improved in color. Reducing agents are sometimes added or special equipment is used. However, the transglycosidation is usually performed in an externally heated stirred tank or in a heated stirred tank cascade.

According to EP-A-0 514 628, the transglycosidation can also be carried out in an evaporator. According to EP-A-0 514 627, the transglycosidation is carried out in a reaction column. A molar ratio of alkyl glycoside having a short alkyl radical to long-chain alcohol of 1:2 to 1:15 is set in this case and alkyl oligoglycosides are obtained having degrees of glycosidation of preferably 1.2 to 3.

WO 93/101 33 describes a two-stage process for preparing alkyl oligoglycosides which can be carried out continuously or discontinuously and in which a glucose syrup having a content of monomeric glucose of 90 to 100% is used. The process described here is highly complex overall. It requires a secondary reaction both in the glycosidation and also in the transglycosidation.

In the transglycosidation here, the fatty alcohol which has been heated to the reaction temperature is introduced into a stirred tank having jacket heating. The short-chain alkyl glycoside is added. During the transglycosidation the mixture is passed into an evaporator at a low vacuum of about 100 mbar.

In the said processes, the heat for the reaction temperature is introduced externally via the reactor jacket.

However, this procedure has the disadvantage that the wall temperature is generally at least 5° to 10° C. above the reaction temperature. This can cause sensitive products to be thermally damaged and discolored at the reactor wall. Encrustations and blockages in the equipment and piping can therefore occur.

The object of the present invention was therefore to avoid overheating, in particular due to elevated jacket temperatures, in the transglycosidation.

SUMMARY OF THE INVENTION

The object is achieved according to the invention by the fact that the fatty alcohol is preheated to at least 80° C., before it is mixed with the $C_2$ to $C_6$ alkyl glycoside, reacted and $C_2$ to $C_6$ alcohol is flashed off under vacuum after the reaction.

DETAILED DESCRIPTION OF THE PREFERRED EMBODIMENTS

Preferably, the fatty alcohol is preheated to 80° to 150° C. and very particularly preferably to 100° to 130° C. The reaction temperature in the transglycosidation is usually 60° to 140° C. and in particular 80° to 120° C.

The flashing, the spontaneous depressurization of the reaction mixture, is generally performed downstream of a throttle point (valve, nozzle etc.). For this purpose a vacuum of 1 to 700 mbar is preferably applied externally. In particular, the absolute pressure in this case is 3 to 40 mbar.

In the preparation of the $C_2$ to $C_6$ alkyl glycosides the monosaccharide used is for example glucose, mannose, galactose, gulose, allose or talose. Preferably, however, glucose is used as starting material here. The alkyl radical is derived, for example, from the alcohols ethanol, n-propanol, isopropanol, n-butanol, t-butanol, amyl alcohol or hexanol. n-Butanol is preferred here, so that for the transglycosidation n-butyl glycoside is preferably used.

To characterize the monosaccharides, the content of reducing sugars, calculated as dextrose on the basis of dry matter, is determined and termed dextrose equivalent. According to this, a pure monosaccharide has a dextrose equivalent of 100, while dextrose equivalents below 100 indicate a content of oligosaccharides. According to the invention, the dextrose equivalent is preferably 90 to 99.8.

The $C_2$ to $C_6$ alkyl glycosides, which can also contain oligomers in small amounts, are used for the transglycosidation preferably dissolved in the associated alcohol. 25 to 60% strength alkyl glycoside solutions are preferably used in this case.

In the flashing, therefore, not only is the alcohol which is formed in the transglycosidation evaporated but also the alcohol which had served as solvent.

The $C_8$ to $C_{20}$ fatty alcohols can be linear or branched. They can also contain olefinic double bonds. Natural or synthetic fatty alcohols or fatty alcohol mixtures can be used. Examples which may be mentioned are octanol, decanol, 10-undecen-1-ol, dodecanol, myristyl alcohol and stearyl alcohol. Preferably, fatty alcohols having 10 to 14 C. atoms are used. The alkyl glycoside having $C_2$ to $C_6$ alkyl groups is usually reacted with the fatty alcohol in a molar ratio of 1:4 to 1:10.

In the transglycosidation the acid catalysts used can be mineral acids such as sulfuric or hydrochloric acid, organic acids are also very suitable, such as arylsulphonic, alkylsulphonic or aralkylsulphonic acids. The catalyst here is preferably introduced into the reaction mixture dissolved or suspended in the preheated fatty alcohol.

The reaction can advantageously be performed in a mixer. The preheated fatty alcohol including the catalyst and simultaneously a $C_2$ to $C_6$ alkyl glycoside solution can be fed into the mixer. The alkyl glycoside solution can also be introduced first and fatty alcohol and catalyst added. However, the transglycosidation can alternatively be carried out in a stirred tank, in a stirred-tank cascade or after previous mixing in a tubular reactor.

The alkyl oligoglycosides prepared according to the invention usually have degrees of glycosidation of 1 to 3. Accordingly, here, even products having the degree of glycosidation 1 are termed alkyl oligoglycosides. The degree of glycosidation is preferably in the range from 1.1 to 1.5 and very preferably in the range from 1.1 to 1.4.

The product of the transglycosidation is neutralized with suitable bases in a known manner. The excess fatty alcohol is then separated off by distillation which can be performed in a thin-layer evaporator or a short-path evaporator. The alkyl oligoglycoside obtained is then mixed with water and bleached with peroxide. The end product has an iodine color value (ICV) of below 20 and preferably has a residual fatty alcohol content of less than 1%.

The process according to the invention of direct heat supply enables the wall temperature of the reactor not to exceed the product temperature of the reaction mixture overheating at the reactor walls therefore does not occur. The process leads to reaction mixtures having a very low content of undissolved constituents. The color quality of the products is improved. Cracking and encrustation do not occur. Piping and reactors therefore do not have a tendency to blockages. This increases the operational safety.

Other features of the invention will become apparent in the course of the following descriptions of exemplary embodiments which are given for illustration of the invention and are not intended to be limiting thereof.

EXAMPLE 1

In a heat exchanger (area: 0.4 m$^2$) 40 kg of $C_{12}/C_{14}$ fatty alcohol and 0.2 kg of butanolic p-toluenesulphonic acid solution (173 g/l p-toluenesulphonic acid) per hour are heated from 40° to 120° C. A 35% strength butyl glucoside solution is then fed in, whereupon the liquids are mixed homogeneously in a static mixer. After the mixture flows through a reaction path (residence time 10 minutes), butanol is flashed off downstream of a control valve at a vacuum of 10 mbar.

After neutralization and distillation of the fatty alcohol in the thin-layer evaporator and bleaching using $H_2O_2$ in aqueous solution, a product is obtained having an ICV (of a 50% strength aqueous solution) of 10.

Obviously, numerous modifications and variations of the present invention are possible in light of the above teachings. It is therefore to be understood that within the scope of the appended claims, the invention may be practice otherwise than as specifically describe therein.

This application is based on German Patent Application P 44 31 853.7, filed in the German Patent Office on Sep. 7, 1994, the entire contents of which are hereby incorporated by reference.

What is claimed and desired to be secured by Letters Patent of the United States is:

1. A process for preparing alkyl oligoglycosides which have $C_8$ to $C_{20}$ alkyl radicals by acid-catalyzed transglycosidation of $C_2$ to $C_6$ alkyl glycosides having $C_8$ to $C_{20}$ fatty alcohols comprising:

a) preheating a $C_{8-20}$ fatty alcohol to at least 80° C.;

b) mixing said preheated $C_{8-20}$ fatty alcohol with an alkyl glycoside and reacting the mixture to form a reaction mixture in a reactor having walls, wherein the temperature of said walls does not exceed the temperature of said reaction mixture; and c) after said reaction, flashing off a $C_2$ to $C_6$ alcohol under vacuum.

2. The process of claim 1, wherein said fatty alcohol is preheated to 80° to 150° C.

3. The process of claim 1, wherein said fatty alcohol is preheated to 100° to 130° C.

4. The process of claim 1, wherein said reaction temperature is 60° to 140° C.

5. The process of claim 1, wherein said reaction temperature is 80° to 120° C.

6. The process of claim 1, wherein said $C_2$ to $C_6$ alcohol is flashed off at 1 to 700 mbar.

7. The process of claim 1, wherein said $C_2$ to $C_6$ alcohol is flashed off at 3 to 40 mbar.

8. The process of claim 1, wherein an acid catalyst is introduced into said reaction mixture dissolved or suspended in said preheated fatty alcohol.

9. The process of claim 1, wherein said alkyl glycoside and $C_{8-20}$ fatty alcohol are used in a ratio of 1:4 to 1:10.

10. The process of claim 1, wherein said alkyl glycoside is used as a 25–60% alkyl glycoside solution.

11. The process of claim 1, wherein said alkyl oligoglycosides produced by said process have a degree of glycosidation in the range from 1.1 to 1.5.

12. The process of claim 11, wherein said degree of glycosidation is in the range from 1.1 to 1.4.

13. The process of claim 1, wherein said alkyl oligoglycosides produced by said process have an iodine color value below 20.

14. The process of claim 13, wherein said alkyl oligoglycosides have a residual fatty alcohol content of less than 1 wt. %.

15. The process of claim 1, consisting essentially of steps a), b) and c).

16. The process of claim 1, consisting of steps a), b) and c).

17. A process for preparing alkyl oligoglycosides which have $C_8$ to $C_{20}$ alkyl radicals by acid-catalyzed transglycosidation of $C_2$ to $C_6$ alkyl glycosides having $C_8$ to $C_{20}$ fatty alcohols comprising:

a) preheating a $C_{8-20}$ fatty alcohol and an acid catalyst to at least 80° C.;

b) mixing said preheated $C_{8-20}$ fatty alcohol with an alkyl glycoside and reacting the mixture; and c) after said reaction, flashing off a $C_2$ to $C_6$ alcohol under vacuum.

* * * * *